US006268386B1

(12) United States Patent
Thompson

(10) Patent No.: US 6,268,386 B1
(45) Date of Patent: *Jul. 31, 2001

(54) NICOTINE BEVERAGE

(76) Inventor: Marshall Anlauf Thompson, 1253 N. Modesto, Camarillo, CA (US) 93010

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 56 days.

(21) Appl. No.: 09/104,225

(22) Filed: Jun. 25, 1998

(51) Int. Cl.[7] .................................................. A61K 31/44
(52) U.S. Cl. ........................... 514/343; 514/810; 514/813
(58) Field of Search ................................ 514/343, 810, 514/813

(56) References Cited

U.S. PATENT DOCUMENTS

| 4,748,181 |   | 5/1988 | Hutchinson et al. | 514/343 |
|-----------|---|--------|-------------------|---------|
| 4,835,162 | * | 5/1989 | Abood             | 514/305 |
| 4,907,605 | * | 3/1990 | Ray et al.        | 131/270 |
| 5,326,563 | * | 7/1994 | Spindler et al.   | 424/197 |
| 5,549,906 | * | 8/1996 | Santus            | 424/440 |
| 5,573,774 | * | 11/1996| Jeenan            | 424/423 |
| 5,747,512 | * | 5/1998 | Keenan            | 514/343 |
| 5,810,018 | * | 9/1998 | Monte             | 131/270 |
| 5,846,983 | * | 12/1998| Sandborn et al.   | 514/343 |
| 6,211,194 | * | 4/2001 | Westman et al.    | 514/300 |

FOREIGN PATENT DOCUMENTS

| 19747138 |   | 4/1999 | (DE) . |         |
|----------|---|--------|--------|---------|
| 88/03803 | * | 6/1988 | (WO)   | 514/343 |
| WO9955371|   | 4/1999 | (WO)   | A61K/47/00 |

OTHER PUBLICATIONS

Zins et al, J. Clin Pharmacol., vol. 37, pp. 426–436, May 1997.*

Schneider et al, Addiction, vol. 91, #9, pp. 1293–1306, 1996.*

* cited by examiner

Primary Examiner—James H. Reamer
(74) Attorney, Agent, or Firm—Koppel & Jacobs

(57) ABSTRACT

A liquid composition including a Nicotine or alkaloid having the same direction of activity, content of between 0.0001% and 0.1% that can be consumed orally.

6 Claims, No Drawings

NICOTINE BEVERAGE

BACKGROUND

Tobacco which contains a natural nicotine content has a enormously large and devoted following. This dedication however carries the price of highly accelerated incident of negative health events. While it is the nicotine in tobacco that people seek it is not the nicotine that is the primary cause of negative health events. It is therefore reasoned that if a product could provide nicotine without the other ingredients of tobacco then the risk of negative health events would also diminish.

BRIEF SUMMARY AND OBJECTIVES OF INVENTION

It is insufficient for a safer nicotine product to be available to the public if the form is unacceptable to current tobacco users. Previous nicotine delivery patents have directed their efforts toward mimicking tobacco method of usage or variations of drug application techniques. The goal of this innovation is to introduce the nicotine by a delivery system which is already utilized by all people, the oral consummation of fluids. To be effective however the fluid must be such that is acceptable to its intended users, preferably one or more that are already established. The majority of consumable fluids available to the public have one of these three fluids as their primary ingredients, water, carbonated water or natural juice.

Therefore, the objective of this innovation is to form a liquid consisting of nicotine or alkaloid having the same direction of activity with one or any combination of water, carbonated water or natural juice and that the resulting composition could be consumed orally. Said composition may also include one or more ingredients to help make it more appealing to the public.

DESCRIPTION

Due to the wide variety of tobacco users any innovation with a goal of reaching this group will need to incorporate a large degree of flexibility into its formula. The first example of this is in the choice of delivery systems chosen for this concept. Water, carbonated water and natural juice cover the preponderance of consumable liquids currently available to the public, thereby making the availability of nicotine from a source other than tobacco as pleasing as possible.

With the delivery system ascertained the next variable is what is a reasonable quantity of nicotine or alkaloid having the same direction of activity, per serving and the size of that serving. To high a content per serving could result in negative health events and since the focus of this invention is to reduce negative health events all be it of a different nature, the goal is still the same. Also contributing to this variable is the taste of the resulting composition. Nicotine has a taste best compared to eating "pepper", to high a content would result in the public not willing to use this innovation and returning to tobacco use with it increased health risks. Similarly to low a content would not delivery the desired effects which could lead to a return to tobacco products. Therefore the most effective nicotine content level would be one similar normal intake of nicotine from tobacco products with a fluid amount sufficient to mask as much of the nicotine taste as reasonable.

The parameters of this invention are between 0.1% and 0.0001% of a liquid composition is made of nicotine or alkaloid having the same direction of activity. This allows the desired portion to meet the needs of the individual be it a serious desire to quell their need for nicotine or a more casual desire for a product that includes nicotine or nicotine like component. Tobacco users are an enormous and dynamic group and it is the flexibility of this concept as much as any component that will allow it to perform as planed.

What is claimed is:

1. A method of delivering nicotine or an alkaloid to an individual to reduce said individual's use of tobacco products comprising providing a beverage with a nicotine or alkaloid having similar physiological activity, the nicotine or alkaloid content being between 0.0001% and 0.1%.

2. A method of delivering nicotine or an alkaloid to an individual to reduce said individual's use of tobacco products comprising providing for oral delivery a liquid composition which includes between 0.0001% and 0.1% of the nicotine or alkaloid having similar physiological activity.

3. The liquid composition of claim 2 wherein the primary constituent of the beverage is water.

4. The liquid composition of claim 3 wherein the water is carbonated.

5. The liquid composition of claim 2 wherein the primary constituent of the liquid composition is a natural fruit juice.

6. The liquid composition of claim 2 wherein the nicotine or alkaloid is a non-naturally occurring material.

* * * * *